United States Patent [19]

Hetrick et al.

[11] 4,396,466

[45] Aug. 2, 1983

[54] ABSOLUTE PRESSURE SENSOR

[75] Inventors: Robert E. Hetrick, Dearborn Heights; William A. Fate, Ann Arbor, both of Mich.

[73] Assignee: Ford Motor Company, Dearborn, Mich.

[21] Appl. No.: 258,150

[22] Filed: Apr. 27, 1981

[51] Int. Cl.³ ............................................. G01N 27/46
[52] U.S. Cl. ....................................... 204/1 T; 204/406
[58] Field of Search ............................. 204/1 S, 195 S

[56] References Cited

U.S. PATENT DOCUMENTS

| | | | |
|---|---|---|---|
| 2,999,379 | 9/1961 | Beard et al. | 73/23 |
| 3,100,868 | 8/1963 | McAfee | 324/33 |
| 3,311,454 | 3/1967 | Kemeny et al. | 23/254 |
| 3,347,635 | 10/1967 | McKee | 23/232 |
| 3,654,112 | 4/1972 | Beekmans et al. | 204/195 S |
| 3,698,384 | 10/1972 | Jones | 204/195 S |
| 3,857,771 | 12/1974 | Sternberg | 204/195 B |
| 3,907,657 | 9/1975 | Heijne | 204/195 S |
| 3,923,624 | 12/1975 | Beekmans et al. | 204/195 S |
| 4,101,403 | 7/1978 | Kita et al. | 204/195 S |
| 4,112,893 | 9/1978 | Anzai | 204/195 S |
| 4,121,548 | 10/1978 | Hattori et al. | 123/32 EE |
| 4,135,381 | 1/1979 | Sherwin | 73/23 |
| 4,147,513 | 4/1979 | Bienkowski et al. | 23/232 E |
| 4,148,211 | 4/1979 | Sawa et al. | 73/23 |
| 4,272,329 | 6/1981 | Hetrick et al. | 204/195 S |
| 4,272,330 | 6/1981 | Hetrick | 204/195 S |
| 4,272,331 | 6/1981 | Hetrick | 204/195 S |

*Primary Examiner*—T. Tung
*Attorney, Agent, or Firm*—Peter Abolins; Clifford L. Sadler

[57] ABSTRACT

This specification discloses an absolute pressure sensor and measuring technique using an electrochemical apparatus as a feedback element in an oscillator circuit. The sensor needs no reference pressure or reference vacuum. Contributing to sustained oscillation is a phase shift caused by the electrochemical apparatus. The period of oscillation of the oscillator circuit is inversely proportional to the diffusion coefficient of oxygen in its carrier gas, which, in turn, is inversely proportional to total absolute pressure. The result is that the period of oscillation of the oscillator circuit is proportional to total absolute pressure.

11 Claims, 6 Drawing Figures

ABSOLUTE PRESSURE SENSOR

BACKGROUND OF THE INVENTION

1. Field of the Invention

This invention relates to a device for measuring absolute pressure.

2. Prior Art

Known absolute pressure sensors include capacitive transducers which provide a variation in electrical capacitance as a function of pressure. The pressure can act upon the "plates" of the capacitive transducer, the aligned areas of such plates, the type of dielectric material between the capacitive plates, and combinations of these. All of these capacitive transducers have the common characteristic that an electrical signal is detected and provides an indication of the magnitude of the capacitance which, in turn, is an indication of the pressure to be measured.

Another characteristic of such capacitive transducers is the need for a reference atmosphere. Such a reference atmosphere, reference pressure, or vacuum is also a characteristic of various other pressure sensors such as those with a diaphragm. Typically, the reference pressure is established on one side of the diaphragm and the pressure to be measured is on the other side of the diaphragm. Movement of the diaphragm causes a physical indication of the pressure to be measured. Although the use of a reference pressure is prevalent in absolute pressure sensors, it is undesirable because it adds to the cost of the sensor. A cost increase is particularly undesirable when many absolute pressure sensors must be produced. For example, current automobile vehicles with advanced fuel metering systems use two absolute pressure sensors, one to measure ambient pressure and one to measure intake manifold pressure. Increased future usage is anticipated. In addition to the cost of initially establishing the reference pressure, reliably maintaining the pressure sensor reference can be a problem. Any break in the integrity of the container or walls defining the reference atmosphere would cause malfunctioning of the output pressure sensor. Such malfunction can, of course, result in customer dissatisfaction. These are some of the problems this invention overcomes.

SUMMARY OF THE INVENTION

An absolute pressure sensor in accordance with an embodiment of this invention needs no reference pressure or reference vacuum. The sensor uses an electrochemical apparatus as a feedback element in an oscillator circuit whose period of oscillation is proportional to total absolute pressure. The apparatus includes two electrochemical cells employing $ZrO_2$ suitably adapted to serve as an oxygen ion conducting solid electrolyte. Alternate oxygen ion conducting solid electrolytes may be used. One of the cells is operated under open circuit conditions to act as a sensor of oxygen partial pressure, while current is passed through the other so that molecular $O_2$ is pumped from one side of the cell to the other. The pump and sensor cells are attached to supporting structure to define an enclosed volume in communication with the ambient atmosphere through a leak orifice. When the enclosed volume is immersed in an ambient environment containing a partial pressure of oxygen, that ambient can establish itself within the volume by means of the orifice.

In operation, a sustained oscillatory mode of the system exists if the pumping and sensing action allows a phase shift between voltage applied to the pump cell and voltage measured at the sensor cell. Contributing to the phase shift is the distance between the pump and sensor cells. That is, an electrical action at the pump cell is delayed from appearing at the sensor cell by the time oxygen takes to diffuse between the pump and sensor cells.

BRIEF DESCRIPTION OF THE DRAWINGS

FIG. 5a corresponds to an absolute pressure of 720 millimeters of mercury and FIG. 5b represents a pressure of 150 millimeters of mercury, the time scale for both being 100 milliseconds per centimeter and the bias voltage $V_R$ being minus 15.5 millivolts.

DETAILED DESCRIPTION OF THE INVENTION

This disclosure teaches a pressure sensor (FIG. 1) and a measurement technique for measuring the absolute pressure in a relatively high temperature gaseous environment such as may be found in automotive engines. In the latter environment, as an example, the electrical output of the device, which can be proportional to ambient pressure or intake manifold pressure, may be used in the feedback control of the air-to-fuel ratio of the automotive engine. The pressure sensor includes an external circuit 30 and a solid electrochemical device 10, which serves as a feedback element for external circuit 30. Electrochemical device 10 is described below and further in U.S. Ser. No. 126,606, filed Mar. 3, 1980, and having inventors and assignee in common with this application. Requirements for device operation include that the gas whose pressure is to be measured must contain some oxygen, e.g., a range of 0.1% to 5% has been used experimentally; and the device must be operated at elevated temperatures, e.g., greater than about 700° C.

Figure 2:
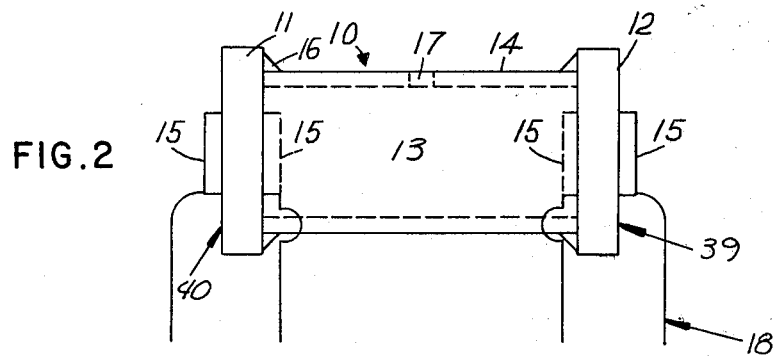
FIG. 2 is a more detailed view of the construction of the electrochemical apparatus in FIG. 1.

As shown in the embodiment of FIG. 2, the device 10 includes two platelets, 11 and 12, of zirconium dioxide suitably adapted for the conduction of $O^=$ ions. Such a solid ionic conductor is called a solid electrolyte. Electrodes 15 are attached to opposing faces of each platelet to form electrochemical cells. The right hand cell is termed the pump cell, and the left hand cell the sensor cell to reflect their functions. The electrodes consist of platinum films (typically applied by common sputtering techniques) with a typical thickness of 1.0 micron, or other material adapted for the purpose. Lead wires 18 are affixed to each electrode so that external circuitry may be applied to the cells. Using glass frits or ceramic glue 16, the zirconium dioxide platelets are joined by a hollow, nonporous ceramic tube 14 to define an enclosed volume 13. The joining is effected so that one electrode from each cell will lie within the enclosed volume. A small hole 17 can be drilled into the ceramic tube or even the cells themselves to allow the ambient atmosphere to establish itself within the volume. Other embodiments may incorporate other $O^=$ conducting solid electrolytes (ex. $CeO_2$ adapted for the purpose) which can perform the desired electrochemical functions at lower temperatures. The device is completely immersed in the atmosphere whose pressure is to be determined.

Figure 1:
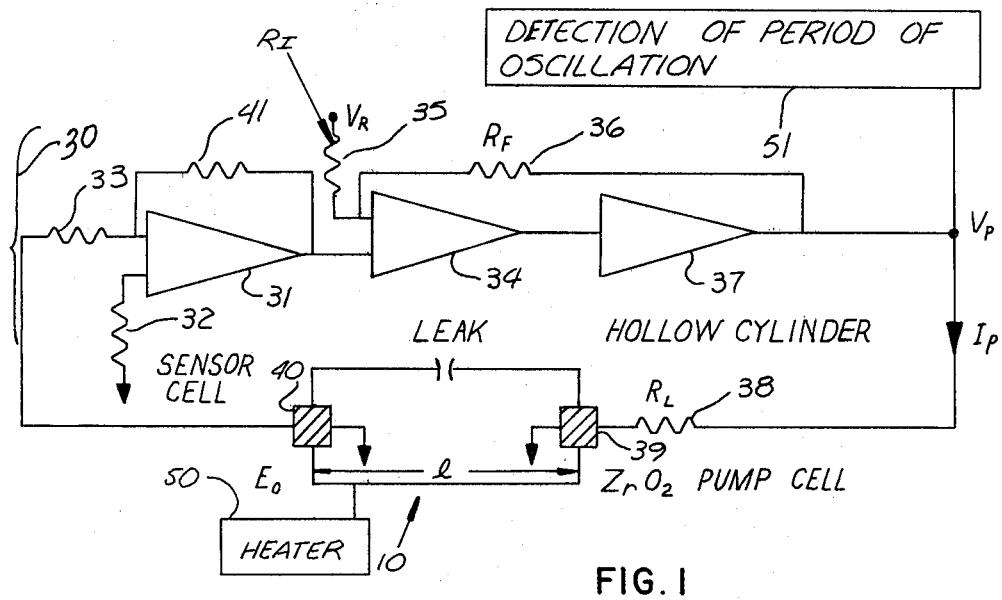
FIG. 1 is a schematic diagram of a pressure sensor means in accordance with an embodiment of this invention including an electrochemical apparatus connected to an external oscillatory circuit.

Electrical operation can be discussed with reference to FIG. 1 which shows device 10 wired to external circuit 30. The purpose of pump cell 39 is to cause gaseous oxygen to be withdrawn from or injected into the volume when external circuit 30 causes a current ($I_p$) to pass through pump cell 39. Due to this pumping action the oxygen partial pressure in the volume is increased or decreased relative to the oxygen partial pressure in the ambient atmosphere. This increase or decrease causes an emf ($E_o$) to be generated across sensor cell 40 which is "read" by amplifier 31. Amplifier 31 is a unity gain high impedance buffer stage which guarantees that sensor cell 40 is monitored under nearly open circuit conditions. The output of amplifier 31 is connected to amplifier 34 which acts as a comparator and subtracts a DC reference voltage ($V_R$) from the buffered sensor cell output. Amplifier 34 is coupled to amplifier 37 which is a current amplifier with sufficiently large current output capability to drive pump cell 39 through current monitoring resistor 38. The AC voltage gain of the two amplifiers 34 and 37 is approximately $R_F/R_I$.

Under DC steady state conditions the circuit 30 is a servo system that controls the sensor output voltage ($E_o$) at a value very nearly equal (depending on gain) to the comparator reference voltage ($V_R$). Operation in this mode has been described in detail in U.S. Ser. No. 126,606 as specified above.

Under certain conditions the composite system (device 10 wired to external circuit 30) can be made to undergo self-excited oscillations. Self-excited oscillations occur at frequencies for which the phase change of a signal traveling once around the servo loop is $2\pi$ radians or 360°. For the configuration shown in FIG. 1, the buffer amplifier 31 gives a phase shift of $\pi$ radians or 180°, and so, for self-excited oscillations to exist, the remainder of the external circuit 30 together with device 10 must contribute a phase shift of an additional $\pi$ radians or 180°. For the configuration shown in FIG. 1, this remaining phase shift must come from device 10. The simplest case exists when the oscillation frequency is low enough that the impedance of the Nernst cells 39 and 40 have no reactive component and correspondingly provide no additional phase shift. Then the required 180° phase shift must be entirely due to the diffusional relay for $O_2$ molecules traversing the gas path interior to device 10. Solution of the diffusion equation shows that sustained oscillations exist at angular frequency $W=2\pi f$ where $$W=11.187(D/l^2) \qquad (1)$$

and D is the diffusion coefficient of oxygen molecules in the gas mixture. Because D is inversely proportional to absolute pressure, oscillation period is proportional to absolute pressure as is observed experimentally. This is the basis for sensor action. Referring to FIG. 1, a detector 51 is coupled to the output of amplifier 37 to detect the period of oscillation and thus the absolute pressure. If desired, detector 51 can correct the measurement of the pressure for dependence of the pressure sensor output on the temperature.

The proportionality constant, 11.187, is determined within the model by the fact that the device must provide a phase shift of $\pi$ radians. Standard electrical components could be added to the external circuit which would produce an additional phase shift. For oscillations to occur, a different phase shift would then be required of the device. In this case a different proportionality constant would be appropriate and oscillations with a period proportional to pressure would occur at different frequencies. In this way the oscillation frequency could be tuned to a desired range if necessary.

Typical components for amplifiers 31 and 34 are CA3140 and for amplifier 37 MC1438; Resistors 32, 33 and 41: 100 k$\Omega$; resistor 35: 1 k$\Omega$; resistor 36: 1 M$\Omega$; resistor 38: 10$\Omega$. In a typical device the length 1 is about 1 cm.

Figure 3:
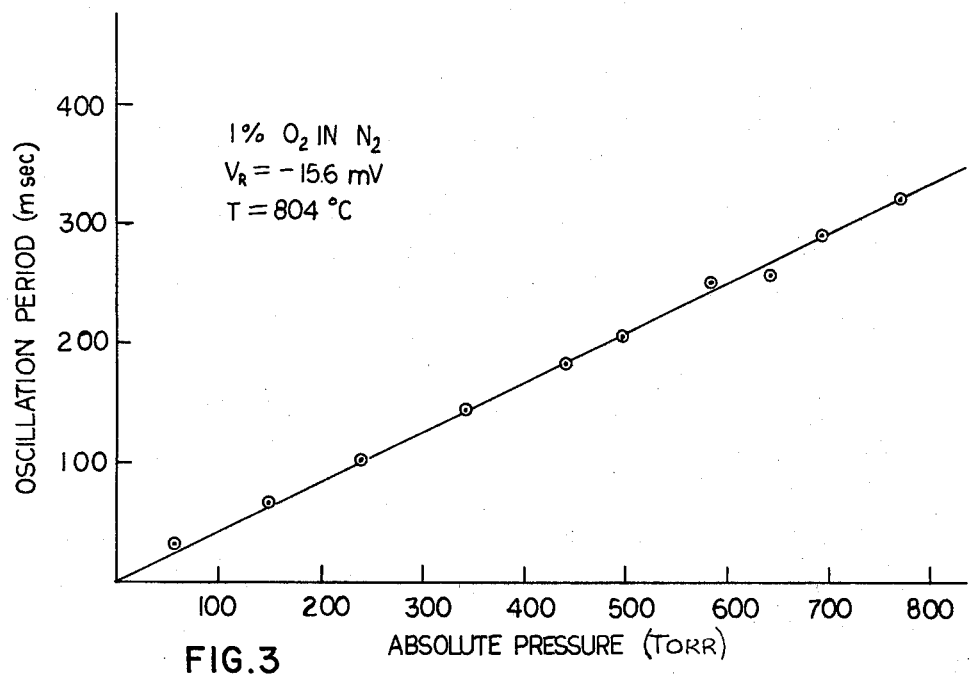
FIG. 3 is a graphical representation of oscillation period versus absolute pressure as measured in accordance with an embodiment of this invention.

FIG. 3 shows period of oscillation versus pressure where the linear dependence of oscillation period on pressure inferred from equation (1) is seen to be valid for pressures greater than about 175 torr. This is the pressure range of automotive interest. It was verified that the departure from linearity at the lowest pressure is accompanied by a phase shift between output voltage $V_p$ and pump current $I_p$. The latter phase shift, associated with electrode processes occurring under the extremes of operating conditions, will also contribute in determining the oscillation period and reduce the sensitivity to pressure.

In the high pressure region one may set $D=D_o/P$ where $D_o$ is independent of pressure and P is pressure. From equation (1), $D_o=2\pi l^2/11.187S$ where S is the slope of the straight line drawn through the high pressure ($>200$ mm Hg) data points in FIG. 3. We find $D_o=1.92$ (cm$^2$/sec) atm in reasonable agreement with known diffusion data for oxygen in nitrogen, such as discussed in C. S. Tedmon, Jr., et al., Journal of the Electrochemical Society, 116, 1170, 1969. This agreement confirms the diffusion mechanism as that responsible for the phase shift.

Figure 4:
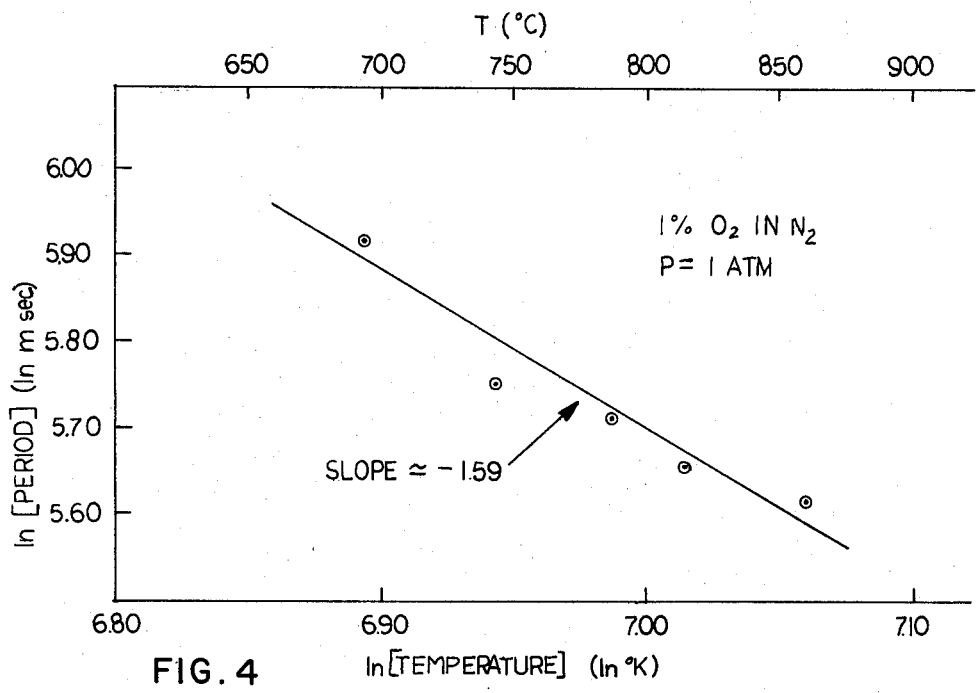
FIG. 4 is a graphical representation of the natural logarithm of the period of the oscillation versus the natural logarithm of the temperature thus showing the temperature dependence of the period of oscillation at one atmosphere total pressure.

FIG. 4 shows the temperature dependence of oscillation period at one atmosphere total pressure. On the basis of kinetic theory calculations one expects the period to vary as $T^{-1.8}$ dependence. (See, for example, E. H. Kennard "Kinetic Theory of Gases", McGraw Hill Book Cp., N. Y. 1938, Sects. 109, 114). The data show an approximate $T^{-1.6}$ dependence. In a practical device, a heater 50 (FIG. 1) will be advantageous to maintain the near constant high temperature required. Heater 50 can maintain device 10 within a temperature range sufficiently small to achieve a desired accuracy.

Figure 5A:
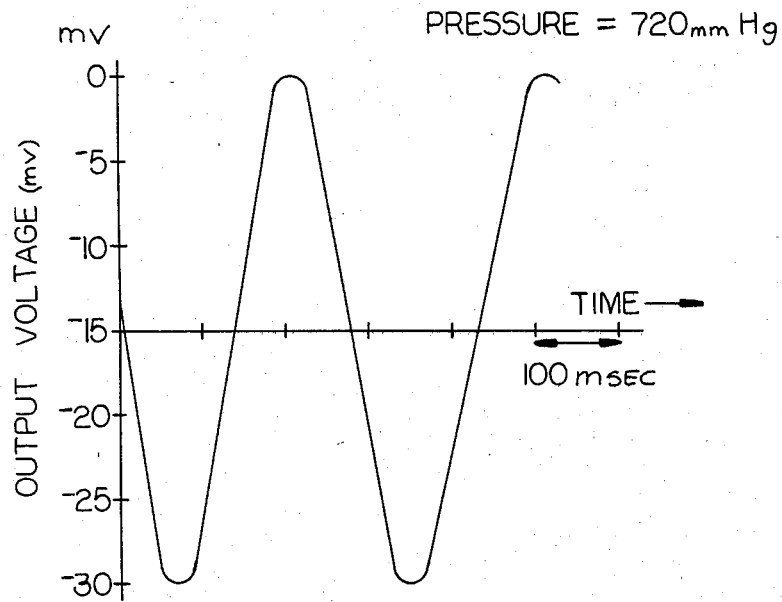
FIGS. 5a and 5b show graphic representations of an oscillating pump voltage versus time.
Figure 5B:
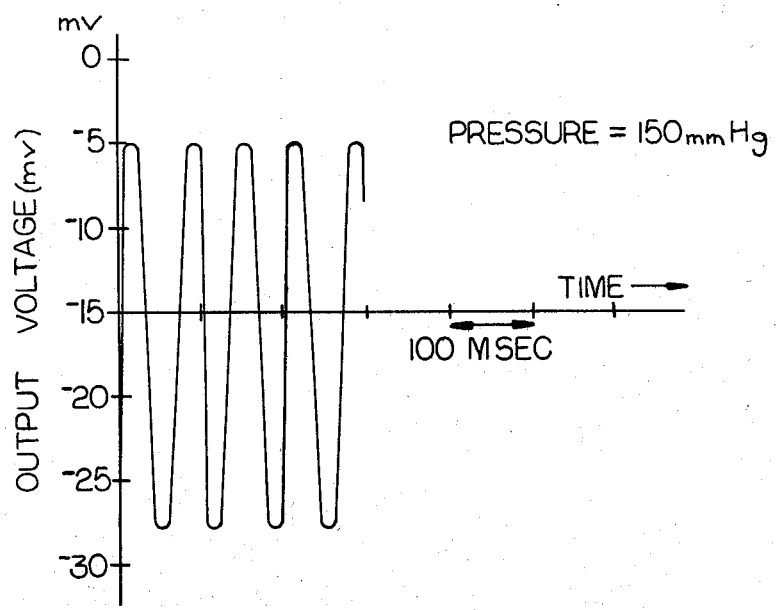

FIGS. 5a and 5b show experimental results wherein the period of oscillation changes with the ambient pressure. The higher pressure of FIG. 5a is associated with a longer period, and the lower pressure of FIG. 5b is associated with a lower pressure.

Various modifications and variations will no doubt occur to those skilled in the various arts to which this invention pertains. For example, the phase shift of the external circuit 30 may be varied by adding components.

Another possible configuration would be to construct the device so it could fit on the end of a spark plug structure for convenient insertion into a vehicle. These and all other variations which basically rely on the teachings through which this disclosure has advanced the art are properly considered within the scope of this invention.

What is claimed is:

1. A pressure sensor means for making a measurement of absolute pressure in an ambient environment including oxygen, said pressure sensor means including an electrochemical apparatus and an external circuit means, said electrochemical apparatus having:

a solid electrochemical pump cell;

a solid electrochemical sensor cell;

an associated supporting structure which in combination with said pump and sensor cells defines an enclosed volume;

a leak orifice for providing communication between said enclosed volume and the ambient environment so that when said enclosed volume is immersed in an ambient environment containing a partial pressure of oxygen that ambient will establish itself within the enclosed volume;

said pump and sensor cells being formed of platelets of solid ionic conductors capable of conducting oxygen ions and including two electrode layers attached to opposing faces of each of said platelets, and lead wire attached to each of said electrodes for coupling said external circuit means to said pump and sensor cells;

said external circuit means having an input and an output, and being coupled to said electrochemical apparatus so that said electrochemical apparatus serves as a feedback element for said external circuit means thus adapting said external circuit means for self-excited oscillation and producing a signal whose period of oscillation is proportional to total absolute pressure;

said external circuit means having said output coupled to said pump cell to cause electrical current to flow in said pump cell for the purpose of withdrawing oxygen from said enclosed volume thereby causing a voltage to be induced across said sensor cell;

said sensor cell being coupled to said input of said external circuit means;

said external circuit means being adapted to enter into self-excited electrical oscillation at the frequency where said electrochemical apparatus causes a 180 degree phase lag between the voltage across said electrode layers of said sensor cell and the voltage applied to said electrodes of said pump cell; and said external circuit means including phase shift means for providing a 180 degree phase shift so that a signal traveling once through said electrochemical apparatus and said external circuit means has a phase shift of 360 degrees, thus permitting self-excited oscillation.

2. A pressure sensor means as recited in claim 1 wherein said external circuit means includes a buffer means to amplify the voltage of said sensor cell for use by said external circuit means as well as to provide a phase shift of 180 degrees between voltages at said input and output of said external circuit means.

3. A pressure sensor means ad recited in claim 1 wherein said external circuit means includes a voltage source means for providing a preset reference voltage, $V_R$, and has an output coupled to said pump cell so as to apply an output signal $V_P$ for withdrawing oxygen from said enclosed volume at a sufficient rate so that an emf, $E_o$, generated across said sensor cell is driven toward the preset reference voltage, $V_R$.

4. A pressure sensor means as recited in claim 3 wherein:

said external circuit means includes the series connection of a buffer means for detecting a voltage, a comparator means for comparing two voltages, and an amplifier means for amplifying a voltage;

said buffer means having an input coupled to said sensor cell and a buffer output;

said comparator means having a first input coupled to said buffer output, a second input coupled to said voltage source means for receiving said reference voltage, $V_R$, and a comparator output; and said amplifier means having an input coupled to said comparator output and an amplifier output coupled to said second comparator input and to said pump cell.

5. A pressure sensor means as recited in claim 4 wherein:

an input resistor, $R_I$, couples said voltage source means to said second comparator input;

said first and second inputs to said comparator means have different signs so said comparator means produces an output proportional to $V_R - E_o$;

a feedback resistor, $R_F$, couples said amplifier output to said second comparator input so that said amplifier means amplifies the comparator output by a factor $R_F/R_I$ to produce said output signal, $V_P$.

6. A pressure sensor means as recited in claim 5 further comprising:

detection means coupled to said external circuit for detecting the period of oscillation of the signal $V_P$ and establishing a proportion between said period and the absolute pressure thereby determining the absolute pressure.

7. A pressure sensor means as recited in claim 6 further comprising a heater means adjacent said pressure sensor means for maintaining said electrochemical apparatus within a temperature range sufficiently small to achieve a desired accuracy.

8. A method for making a measurement of absolute pressure in an ambient environment including oxygen, said method including the steps of:

establishing an enclosed volume with restricted access to the ambient environment, the enclosed volume being bounded by a solid electrochemical pump cell and a solid electrochemical sensor cell including a solid oxygen ion conductor, and the restricted access being sufficient so that when the enclosed volume is immersed in an ambient environment containing a partial pressure of oxygen that ambient will establish itself within the enclosed volume;

maintaining a preset voltage magnitude in an external circuit;

using the enclosed volume, pump cell and sensor cell as a feedback element for the external circuit where the output of the external circuit is applied to the pump cell to withdraw oxygen from the enclosed volume to an extent which includes a voltage across the sensor cell equal to the preset voltage magnitude maintained in the external circuit; and detecting an electrical signal generated by the sensor cell in response to the electrical signal at the pump cell and applying it as an input to the external circuit;

said step of using the enclosed volume, pump cell and sensor cell as a feedback element for the external circuit causing the external circuit to break into self-excited oscillations at a frequency where the sum of the phase shift between the voltage applied to the pump cell and the voltage induced on the sensor cell and the phase shift caused by the external circuit equals 360 degrees, so that the period of such oscillations are proportional to the absolute pressure of the ambient environment.

9. A method for making a measurement of an absolute pressure as recited in claim 8 wherein the step of using the enclosed volume, pump cell and sensor cell as a feedback element for the external circuit includes the steps of:

applying an output, $E_o$, of the sensor cell to a buffer means;

applying the buffer output to the first input of a comparator;

applying a reference voltage, $V_R$, to the second input of the comparator;

generating a comparator output proportional to $V_R - E_o$;

applying the comparator output to the input of an amplifier;

applying the output of the amplifier through a resistor $R_F$ to the second input of the comparator;

amplifying the comparator output by a factor $R_F/R_I$ to produce an output voltage $V_p$;

applying the output voltage $V_P$ to the pump cell; and determining the period of oscillation of output voltage $V_P$ thereby establishing absolute pressure.

10. A method as recited in claim 9 further comprising the step of:

maintaining the temperature of the enclosed volume and adjacent regions within a sufficiently narrow range of values so that a predetermined accuracy of the pressure measurement can be maintained with the use of a single calibration constant appropriate for the range of temperatures.

11. A method as recited in claim 10 further comprising the step of:

measuring the temperature in the region of the sensor cell and correcting the measurement of the pressure for the dependence of the pressure sensor output on the temperature.

* * * * *